US011974797B2

(12) United States Patent
Fischer et al.

(10) Patent No.: US 11,974,797 B2
(45) Date of Patent: May 7, 2024

(54) SURGICAL INSTRUMENT HAVING A POSITION DETECTION DEVICE

(71) Applicant: Erbe Elektromedizin GmbH, Tuebingen (DE)

(72) Inventors: Klaus Fischer, Nagold (DE); Alexander Neugebauer, Moessingen (DE); Jan Jaeger, Tuebingen (DE); Bjoern Seitz, Pfullingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 295 days.

(21) Appl. No.: 17/166,502

(22) Filed: Feb. 3, 2021

(65) Prior Publication Data

US 2021/0236187 A1  Aug. 5, 2021

(30) Foreign Application Priority Data

Feb. 5, 2020 (EP) .................................. 20155627

(51) Int. Cl.
*A61B 18/04* (2006.01)
*A61B 1/018* (2006.01)
(Continued)

(52) U.S. Cl.
CPC ............ *A61B 18/042* (2013.01); *A61B 1/018* (2013.01); *A61B 1/07* (2013.01); *A61B 5/065* (2013.01);
(Continued)

(58) Field of Classification Search
CPC ............ A61B 5/065; A61B 2017/0003; A61B 2034/2055
See application file for complete search history.

(56) References Cited

U.S. PATENT DOCUMENTS 5,720,745 A    2/1998  Farin et al.
10,085,616 B2 * 10/2018 Takemoto ............ A61B 1/0016
(Continued)

FOREIGN PATENT DOCUMENTS

CN    102128812 A    7/2011
CN    104602754 A    5/2015
(Continued)

OTHER PUBLICATIONS

Extended European Search Report dated Jul. 23, 2020, in corresponding European Application No. 20155627.1, with machine English translation (14 pages).
(Continued)

*Primary Examiner* — Oommen Jacob
(74) *Attorney, Agent, or Firm* — Fitch, Even, Tabin & Flannery LLP (57) ABSTRACT

A surgical working instrument (3) is disclosed that is inserted in a working channel (7) of an endoscope (2) and is slidably located therein. A device (27) for determination of the relative position of the working instrument (3) to the endoscope (2) is configured to determine in an optical manner that the distal end (8) of the working instrument (3) has reached a distal end (8) of the working channel (7). The position determination device (27) comprises a light conductor (28) that is attached to the working instrument (3) and configured to receive light surrounding the working instrument (3) in the vicinity of its distal end (14), wherein based on the light received by the light conductor (28) the relative position of the light conductor (28) and thus the working instrument (3) in relation to the endoscope (2) can be determined.

23 Claims, 7 Drawing Sheets

(51) Int. Cl.
    *A61B 1/07*     (2006.01)
    *A61B 5/06*     (2006.01)
    *A61B 17/00*     (2006.01)
    *A61B 18/00*     (2006.01)

(52) U.S. Cl.
    CPC ............... *A61B 2017/00061* (2013.01); *A61B 2018/00589* (2013.01); *A61B 2018/00773* (2013.01); *A61B 2018/00982* (2013.01)

(56) References Cited

U.S. PATENT DOCUMENTS

| | | | |
|---|---|---|---|
| 10,456,020 B2* | 10/2019 | Iwasaka | A61B 1/00087 |
| 2006/0052774 A1* | 3/2006 | Garrison | A61B 17/22012 |
| | | | 606/49 |
| 2006/0217594 A1 | 9/2006 | Ferguson | |
| 2009/0123111 A1* | 5/2009 | Udd | G01D 5/35303 |
| | | | 385/13 |
| 2009/0137952 A1* | 5/2009 | Ramamurthy | A61B 5/06 |
| | | | 604/95.01 |
| 2009/0209809 A1* | 8/2009 | Schaller | A61B 1/018 |
| | | | 600/103 |
| 2010/0152538 A1 | 6/2010 | Gleason et al. | |
| 2010/0179414 A1 | 7/2010 | Kuhn et al. | |
| 2010/0179417 A1 | 7/2010 | Russo | |
| 2010/0198244 A1 | 8/2010 | Spivey et al. | |
| 2012/0182409 A1* | 7/2012 | Moriyama | A61B 1/000094 |
| | | | 382/128 |
| 2013/0072753 A1* | 3/2013 | Zappia | A61B 1/0008 |
| | | | 600/104 |
| 2013/0310645 A1* | 11/2013 | Desjardins | A61B 1/267 |
| | | | 600/113 |
| 2015/0090880 A1* | 4/2015 | Andersen | G01N 21/35 |
| | | | 250/339.01 |
| 2018/0206703 A1 | 7/2018 | Zappia et al. | |
| 2019/0142523 A1 | 5/2019 | Govrin | |
| 2021/0236187 A1* | 8/2021 | Fischer | A61B 17/00234 |

FOREIGN PATENT DOCUMENTS

| | | |
|---|---|---|
| CN | 104825121 A | 8/2015 |
| DE | 4139029 C2 | 5/1996 |
| DE | 19731931 A1 | 2/1999 |
| DE | 102004039202 B3 | 1/2006 |
| JP | 2008-508969 A | 3/2008 |
| JP | 2012-143391 A | 8/2012 |
| JP | 2012-217627 A | 11/2012 |
| JP | 2013-244313 A | 12/2013 |
| RU | 2684021 C2 | 4/2019 |
| WO | 94/15533 A2 | 7/1994 |
| WO | 00/00091 A1 | 1/2000 |

OTHER PUBLICATIONS

Russian Patent Office; Office Action in corresponding Russian Patent Application No. 2021 102 085, dated Nov. 22, 2023 (relevant parts translated); 15 pages.

National Intellectual Property Administration, P.R. China, Search Report in corresponding Chinese Application No. 202110160600.4, dated Jan. 30, 2024; 6 pages.

National Intellectual Property Administration, P.R. China, Office Action in corresponding Chinese Application No. 202110160600.4, dated Jan. 30, 2024, 87 pages.

Japanese Patent Office, Notice of Reasons for Refusal in corresponding Japanese Patent Application No. 2021-015593, dated Mar. 15, 2024, 13 pages.

* cited by examiner

SURGICAL INSTRUMENT HAVING A POSITION DETECTION DEVICE

RELATED APPLICATION(S)

This application claims the benefit of European Patent Application No. 20155627.1, filed Feb. 5, 2020, the contents of which are incorporated herein by reference as if fully rewritten herein.

TECHNICAL FIELD

The present invention refers to a surgical instrument for insertion in a working channel of an endoscope having a device for determination of the relative position of the working instrument relative to the endoscope.

BACKGROUND

A device for coagulation of biological tissue, particularly in the gastrointestinal tract, is known from DE 41 39 029 C2, in which a connection cable for connection to an RF-voltage source is provided in a working channel of an endoscope. Gas that can be ionized, e.g. argon, is supplied through the working channel that exits at the distal end of the working channel. An electrode is provided in the flow path of the gas before the exit from the exit opening that serves for ionizing the gas and the supply of the coagulation current. The ionized gas allows the creation of a spark (electric arc) between the electrode and the tissue surface, wherein diseased tissue is scabbed up to a depth of some millimeters due to the heat created thereby.

In the known argon plasma coagulation (APC) device the active electrode is arranged at a defined distance to the endoscope end. An excessive thermal stress of the endoscope end by the created heat can thus be avoided. However, also known are APC devices with a movable APC probe as working instrument that is inserted in the working channel of an endoscope and advanced therein up to the desired working position in which the active electrode slightly projects beyond the distal end of the endoscope. A certain minimum distance between the electrode and the distal end of the endoscope is important in order to avoid that the distal end of the endoscope and components attached thereon, e.g. an observation optic or CCD camera, an illumination device for the area to be treated and the like, are thermally stressed by the heat created during the APC coagulation in an unallowed manner and are damaged. For this a device for detection of the relative position of the electrode relative to the endoscope tip is helpful.

Also for other endoscopic applications with an insertable working instrument comprising an light conductor, as for example for the optical emission spectroscopy (OES), video endoscopy, for rigid laparoscopes, borescopes, fiberscopes and other endoscopes for guide of instruments in the inside of a human body, a position detection for the working instrument could be helpful in order to position the light conductor at a desired distance from the distal end of the endoscope, for example, and to avoid contamination of the light conductor by fluid, blood or tissue particle rests during contact with tissue, e.g. the mucosa of a hollow organ. Such a contamination of the light conductor can result in scattering, absorption or a degradation of the transmission of the light and thus affect the endoscopic sessional treatment.

An endoscope with a used working instrument for argon plasma coagulation that is slidable inside the endoscope together with the electrode is known from DE 197 31 931 A1. In order to use the working instrument for a contact coagulation as well as for a noncontact coagulation and/or for cutting and to thereby reduce the danger of injuries and modifications of the present tissue, a sensor is provided in the area of the distal end that monitors whether the active electrode of the working instrument is located inside or outside of the endoscope catheter. A spring-biased microswitch contact on the distal end of the working instrument, a miniature light barrier, the beam of which is interrupted during presence of the active electrode, or a plate, coaxial or cylinder capacitor, the dielectric of which is influenced due to the presence of the active electrode, can be used as sensor. The non-contact mode can only be activated, if the active electrode is located inside the endoscope catheter.

The position determination requires additional components that have to be provided at the distal end of the working instrument, connections to the distal end, in order to supply electrical or optical measurement signals to the sensor and an appropriate evaluation of the signals provided by the sensor. The effort for the implementation and evaluation is remarkable.

DE 10 2004 039 202 B3 describes a device for measurement of a relative position of a surgical working instrument, wherein the position determination is carried out by means of a measurement of a complex resistance between the working instrument and the working channel of an endoscope or alternatively by means of a pneumatic or acoustic measurement system. For measurement of the complex resistance the endoscope or at least its working channel has to be configured electrically conductible. For an acoustic or pneumatic measurement a measurement signal in form of a sound signal or a balanced or alternating pressure of a gas has to be created and either coupled in the working channel of the endoscope or in a lumen of the working instrument and has to be detected at the respective other of the working channel and the lumen by means of an electromechanical converter or a pressure sensor. This can be relatively elaborate.

A further need of a simple determination of the position of a working instrument relative to a working channel of an endoscope, in that the instrument is inserted, still exists.

Starting therefrom it is an object of the present invention to provide a detection device for the relative position of a surgical instrument relative to a working channel of an endoscope with simple means and low effort for the implementation and the evaluation.

Particularly, it is an object of the invention to provide a surgical instrument for insertion in a working channel of an endoscope, in which the working instrument is slidably arranged, having a device for detection of the relative position of the working instrument relative to the endoscope that allows an adjustment of the working position of the working instrument relative to the endoscope for the respective application with simple means, with low effort for the implementation and the evaluation, such that a thermal impairment of the distal end of the endoscope, a contamination of an light conductor and/or a danger for the patient or the user can be avoided or at least highly reduced.

SUMMARY

For solving this object, according to the invention, the surgical working instrument is provided having the features described herein.

The surgical working instrument for insertion in a working channel of an endoscope, in which the working instrument is slidably arranged, is provided with a device for detection of the relative position of the working instrument relative to the endoscope, wherein the position determination device comprises an light conductor that is anchored on the working instrument and configured to receive light that surrounds the working instrument in the proximity of a distal end, wherein the relative position of the working instrument relative to the endoscope can be determined by means of the light received by the light conductor.

The invention is based on the perception that a light conductor can be included in the working instrument and anchored thereon, such that during insertion of the working instrument in the working channel of an endoscope it is inserted and slid therein together with the working instrument, wherein the light conductor is arranged such that it received the light at the distal end directly or indirectly and wherein the position of the working instrument can be determined by means of the light. Based on the type, intensity, frequency, presence and/or absence of the received light, it can be determined whether and where applicable how far the working instrument is inserted in the working channel of the endoscope and whether it has reached the desired working position. The position detection operates contactless and thus requires no special electric or mechanical components, particularly no contact switches on the distal end of the endoscope. Also no special measurement signals, such as current, voltage, optical, acoustic or pneumatic signals have to be specifically created and have to be introduced through the working instrument to allow the evaluation of the relative position. Further no modification of the endoscope is required.

Rather the light conductor can be simply arranged on the working instrument, such that the position of the light conductor that is determined by means of the received light, characterizes the position of the working instrument.

Preferably the light conductor can comprise a cheap optical fiber, particularly glass fiber or an optical fiber based on plastic, e.g. a polymer optical fiber.

The optical fiber can extend originating from a location in the proximity of the distal end of the working instrument up to a proximal end of the working instrument in order to transmit the light received by the light conductor for evaluation to the proximal end of the working instrument.

In preferred embodiments of the invention the working instrument comprises a tube, particularly a rigid tube or preferably a flexible hose that can consist of an opaque material, if required, however not necessarily, wherein the position determination device comprises a light entering surface that is arranged on the outer side of the tube and is configured for lateral light reception of the light surrounding the distal end of the working instrument. In doing so, an at least nearly total darkening is achieved in the inside of the working channel of the endoscope until the working instrument leaves it, which allows a good detectability of the exit of the working instrument out of the working channel.

Basically, as an alternative, it is also possible to detect light in axial direction, wherein the laterally orientated light detection, however, allows a simpler and better adjusted, more precise position detection.

In a preferred embodiment the light conductor, e.g. the optical fiber, extends substantially in the inner channel (lumen) of the tube of the working instrument along its longitudinal extension, wherein the light entering surface is formed by a face of the light conductor that is laterally lead out of the tube. The realization is simple and the light conductor is housed in the inside of the tube in a protected manner. The light conductor can preferably freely extend in the inner channel of the tube or can be at least attached in sections on the inside of the inner channel.

In another embodiment the light conductor is substantially attached on the outside of the tube and extends along its longitudinal extension from the distal end up to the proximal end of the tube. The light entering surface can be formed by a beveled face (fiber bevel) of the light conductor. The realization is also easy, whereby the attachment of the light conductor, e.g. the optical fiber, at the outside of the tube is simpler.

In another embodiment the light entering surface is formed by a longitudinal glass rod that is separate from the light conductor. The glass rod that preferably consists of silicate glass or acrylic glass, is attached on the outer side of the tube and comprises a certain length that is longer than the width of the glass rod. The length can be longer than the half projection length of the distal end of the working instrument in the desired working position. The glass rod serves for reception of the light surrounding the outer side and the conduction of the received light to the light conductor that is connected with an end of the glass rod facing away from the distal end of the working instrument for light reception and light transmission.

Due to the enlarged dimension of the glass rod in longitudinal direction of the tube, it is possible to detect different amounts or intensities of the surrounding light, depending on how far the glass rod extends beyond the distal end of the endoscope to the outside and is thus subject to the light. In doing so, a precise determination of the position of the working instrument is possible.

In each of the embodiments the light conductor could also be embedded already during extrusion of a PTFE hose of the working instrument on the inner or outer side of the house or inside the hose wall selectively.

Independent from the embodiment, the inventive position determination device is—apart from the light conductor and if appropriate the separate light reception element, such as for example the glass rod—free from lenses, mirrors or other optical elements for redirecting of the light beam detected radially or laterally relative to the longitudinal axis of the working instrument in direction toward the light conductor extending longitudinally along the working instrument. Thus, the position determination device can be realized with little and relatively simple, cheap means, such that it is also suitable for working instruments, such as for example endoscopic probes, that are determined for single use and have to be disposed after use.

The surgical working instrument can in addition comprise an evaluation device that can be connected or is connected to the proximal end of the working instrument and is configured to receive and evaluate the light received and conducted by the light conductor in order to determine the relative position.

In advantageous embodiments the evaluation device can comprise an optical spectrometer unit that is configured to divide the received light in its spectral components in order to be able to determine the spectrum of the received light, i.e. the intensity of the light over a range of light frequencies or in certain discrete frequencies. For example, the spectrometer unit can be based on a light refracting prism or on a light diffracting grid. The evaluation unit can in addition comprise an electrooptical converter, a photodiode array or another suitable device in order to convert the spectrally divided light in respective electrical signals that can be evaluated or analyzed in order to determine the frequency spectrum of the received light signal. The frequency spectrum analysis can also be carried out based on a Fourier-analysis, for example.

A continuous frequency spectrum can be determined for substantially the whole frequency range of the received light, only in individual frequency bands or also only in predefined discrete frequencies.

The evaluation device can in addition comprise a spectrum analyzing unit that is configured to compare the determined intensity of the light over a range of light frequencies or in certain discrete frequencies with stored intensity values of reference spectra and to classify or identify the light received by the light conductor based on the comparison. Particularly a reference spectrum of the illumination light of the endoscope, e.g. a cold light source, can be stored beforehand in order to be used during the evaluation by the spectrum analyzing unit. Also, at least one general reference spectrum for ambient light in a treatment room, in which the endoscope is used together with the surgical working instrument, can be predefined and stored. In addition, it is possible to detect the actual ambient light in the treatment room during start-up, calibration or the maintenance of a surgical apparatus, to convert it in an associated reference spectrum and to store the latter for subsequent analysis by means of the evaluation device. In any case, intensity conditions in different characteristic frequency ranges, bands or lines for the light received by the light conductor can be determined in comparison with the predefined stored reference spectra.

The spectrum analyzing unit can be configured to at least distinguish between a treatment room ambient light that is detected when the surgical working instrument is located outside the endoscope, an at least nearly complete darkness, that is detected when the surgical working instrument is inserted in the working channel of the endoscope, but does not yet project with its distal end out of the working channel of the endoscope, and a treatment light or surgery light from the endoscope that is detected, when the distal end projects so far out of the working channel of the endoscope in the area to be treated in the inside of a patient, such that the light entering surface and the light conductor detect the treatment or surgery light provided by the endoscope.

The spectrum analyzing unit can thus be configured to distinguish between multiple light sources, particularly the cold light source of an endoscope, an ambient light and if necessary, also light emitted from a plasma during the coagulation. While ambient light has wavelengths in the visible range, i.e. between about 400 nm and 800 nm, the working light of a cold light source of the endoscope has in general a characteristic spectrum in the range of 400 nm to 700 nm, while the light emitted from a plasma shows characteristic spectral components between 200 nm and 400 nm, but also components in the visible frequency range. The different characteristic spectral progresses, components or lines allow a reliable distinguishability of the detected types of light by means of the spectrum analyzing unit.

Also, the evaluation device can comprise a detector unit that is configured to detect during insertion of the working instrument in the working channel of the endoscope, when the light entering surface of the position determination device is subject to the environment of a treatment room, enters from the environment of the work room in a proximal end of the working channel or exits the working channel in a body area to be treated and to generate respective position detection signals based on this recognition. The position detection signals can then be transmitted for further use to a superordinate control for the surgical working instrument and/or the endoscope.

In a particularly preferred embodiment with utmost low complexity the evaluation device comprises a detector device that is configured to detect whether light having a minimum intensity is received by the light conductor or not and to generate position detection signals based thereon, that can characterize that the distal end of the working instrument is located outside or inside the working channel of the endoscope. For this the evaluation device can comprise a means, e.g. a photodiode, for conversion of the received light signal in an electrical signal and a detector unit (light-dark detector) that can compare the strength of the electrical signal, e.g. with a predetermined threshold in order to determine whether the signal characterizes light or darkness. A change from light to dark or vice versa can be detected. This allows a superordinate control or a user to determine based on the knowledge about the actual operation progress whether the working instrument is in the treatment room environment, in the working channel of the endoscope or in the desired working position. With the light-dark sensor specific functions of the working instrument can be very easily automated, such as for example initiating a minor inert gas flow (e.g. argon) during the insertion of the working instrument in the endoscope for purposes of clean-keeping or blocking of RF-signals until the instrument is in the correct position. A spectral analysis and a more precise position determination are not required for this.

In particularly advantageous embodiments of the invention the evaluation device based on a light-dark sensor can be integrated in an integral connector, a plug or a socket arranged on a proximal end of the working instrument and provided for connection to an external control apparatus and can directly output electrical signals to the control apparatus that can be used for automatic control. This embodiment is particularly suitable for single use probes, because the evaluation device can be realized extremely cheap and can be disposed together with the working instrument after single use.

If the evaluation device is configured more complexly, having the spectrometer unit and the spectrum analyzing unit, it can also be implemented in a processor-based manner. Some functional parts of the evaluation device, as e.g. the detector unit, can thereby be installed in a connector of the surgical working instrument that serves as interface between the surgical working instrument and a superordinate control apparatus, while other functional parts that are related for example to the storage and evaluation of data or signals can be integrated in the external control apparatus.

In any case, an additional control for the working instrument and/or the endoscope can be provided that is connected or can be connected with the evaluation device and that is configured to automatically initiate measures based on the position detection signals (light-dark sensor signals in the simplest case) transmitted from the detector unit. For example, the control can release the supply of an inert gas, e.g. argon, to the working instrument for keeping it clean, if this is desired or necessary, upon receipt of a first position detection signal that characterizes the start of the insertion of the working instrument in the endoscope. In addition, in this state a pre-activation can be carried out during which the surgical apparatus is parameterized for the subsequent treatment. For example, the necessary RF-voltage and the coagulation current can be preselected and the treatment or surgery illumination of the endoscope can be switched on during the use for coagulation. Preferably an activation lock is effectuated that avoids an undesired ignition of a plasma discharge for ionization of a gas jet and thus an undesired electrical arcing until the surgical working instrument is located in the desired working position relative to the endoscope. Thus, it can be avoided that, due to a direct proximity of the endoscope end to the tissue surface to be treated, an electrical arcing already occurs if the electrode of the working instrument is still inside the working channel of the endoscope or projects only slightly therefrom, because the body and further components of the endoscope, such as for example observation and illumination devices, could be damaged by the heat created thereby.

If the control receives another position determination device from the detector unit that indicates that the distal end of the working instrument, e.g. with the electrode, has reached the desired working position, i.e. the desired distance to the distal end of the endoscope for the treatment, the control can automatically cancel the activation lock and subsequently effectuate the application of the necessary RF-voltage on the electrode and the supply of the necessary coagulation current, the supply of inert gas with the required pressure, if it has not yet happened, the control of a fluid flow or another control of the operation of the working instrument and/or the endoscope.

In a preferred application the surgical working instrument is an argon plasma coagulation (APC) probe for RF-coagulation of biological tissue by means of a flexible endoscope. Then the probe comprises a tube in the form of a flexible hose or an electrically non-conducting material, e.g. polytetrafluoroethylene (PTFE), through which an inert gas, particularly argon, can be supplied and an electrode arranged on the distal end of the tube to which an RF-coagulation current for ionization of the gas can be supplied via a connection conductor that extends in the inner channel of the tube.

The surgical working instrument can also be configured for other purposes, e.g. diagnostic endoscopic purposes, for videoscopes, endoscopes, gastroscopes, bronchoscopes, colonoscopes, hysteroscopes, cystoscopes, arthroscopes, cardiac catheters, boroscopes, fiberscopes, laparoscopes, and the like, also for hyperthermia applications, etc., wherein the position determination device always allows to position a head on the distal end of the working instrument during the treatment, surgery or session in the desired relative position in relation to the endoscope.

Also an indication device can be provided that is configured to indicate the position detection signals output from the detector unit in optical, acoustic, tactile or another manner to a user in order to indicate the user to the respective position of the working instrument. The user can then manually take the necessary measures for control of an operation of the working instrument or endoscope.

The invention allows to determine the relative position of a surgical working instrument relative to the endoscope in a simple manner with low effort for realization and evaluation in order to, for example, avoid damages of the endoscope during a coagulation to comply with allowed thermal stresses on the distal end of the probe as well as the endoscope and/or to avoid contact with the tissue to be treated resulting in contamination of an optical fiber. Due to the light conductance of the light conductor and the relatively quick evaluation only short delay durations are created. Cheap components are used that are particularly suitable for single use probes, particularly with the use of the light-dark detector installed in the connector. No contact switches, no light barriers, no other means to which measurement signals have to be supplied specifically and no shunt resistances are required in the measurement circuit.

BRIEF DESCRIPTION OF THE DRAWINGS

Further preferred details of embodiments of the invention are apparent from the dependent claims, the drawings as well as the corresponding description. The invention is explained in more detail based on the drawings that show exemplarily, but in no way limiting embodiments of the invention, wherein the same reference numerals are used in all figures in order to characterize same elements. The drawings show:

DETAILED DESCRIPTION

Figure 1:
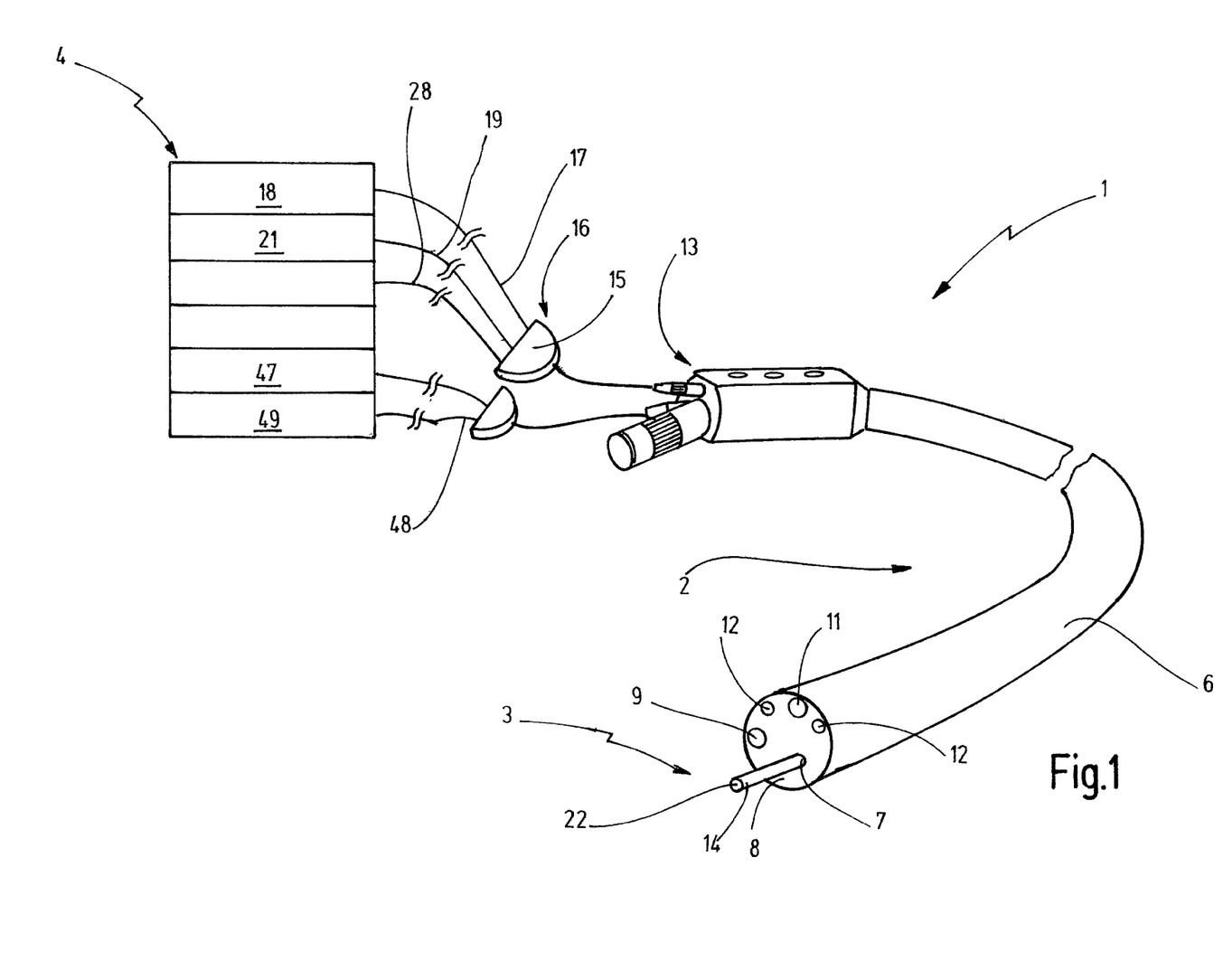
FIG. 1 a medical apparatus having an endoscope and a working instrument inserted therein according to the invention in a highly schematic perspective illustration.

FIG. 1 is a highly schematic illustration of an endoscope system 1 according to an embodiment of the invention having a flexible endoscope 2, a working instrument 3 inserted into the endoscope 2 and a control apparatus 4. The endoscope system 1 is provided in the present example for carrying out an argon plasma coagulation (APC) for stopping hemorrhage from lesions (injuries) particularly of the gastrointestinal tract, whereby the invention can also be used in other medical-endoscopic systems. For example, while a flexible endoscope 2 is illustrated here, in other applications also a rigid endoscope 2 can be used. The inventive endoscope system 1 can be used for multiple other treatments or surgeries, e.g. for desiccation of a tissue surface, eradication of rests of a polypectomy, for tumor scabbing or for thermal tissue marking.

Here the endoscope 2 comprises a longitudinal, bendable tube or a flexible hose 6 of a suitable biocompatible flexible material, particularly polymer material, such as for example polytetrafluoroethylene (PTFE), that is suitable for use in the inside of a patient body. The hose 6 defines a working channel 7 in which working instruments can be inserted. Here, for example, the surgical working instrument 3 is slidably located in the working channel 7 of the endoscope 1, whereby it projects from the distal end 8 of the endoscope 2 that is configured to be inserted into a patient body, from the working channel 7 to the outside. On the distal end 8 in addition, an optional additional working channel 9 is guided out that can be used for other working instruments if needed.

Also a lens or observation device 11 is arranged on the distal end 8 of the endoscope 2 that can comprise a CCD camera or can be connected with an ocular device that is not illustrated here via a glass fiber bundle.

In addition, the endoscope 2 comprises an illumination device 12 with illuminants that project on the distal end 8 of the endoscope 1 to the outward and are connected with a light source, preferably a cold light source via an optical fiber, in order to receive light of high intensity in the visible spectral range and to direct it on a not illustrated treatment or surgery area in the inside of a patient during use. In doing so, an observation of the treatment or surgery area is allowed by means of the observation device 11, including capturing of pictures by means of a CCD camera, while heat creation as with usual light sources is avoided due to the cold light.

The working instrument 3 can be inserted in a proximal end 13 of the endoscope 2 so far, until it exits from the distal end 8 of the working channel 7, as illustrated in FIG. 1. In this position the distal end 14 of the working instrument 3 is located in the field of view of the observation device 11 of the endoscope 2 illuminated by means of the illumination device 12.

A proximal end 16 of the working instrument 3 is connected to the control apparatus 4 by means of a connector or plug 15. The connector 15 comprises a gas supply line 17 via which the working instrument 3 is in flow connection with a gas supply device 18 of the control apparatus 4. The gas supply device 18 is connected with gas stock, e.g. a gas bottle containing argon, and configured to supply the gas, e.g. argon, with a predefined pressure that is suitable for the respective treatment to the working instrument 3.

Also the connector 15 comprises an electric connection conductor 19 via which the working instrument 3 is electrically conductively connected with a radio frequency (RF) generator device 21 of the control apparatus 4, in order to obtain a required RF-voltage therefrom for ignition of a plasma discharge for ionization of the inert gas, e.g. argon, for supply of a coagulation current to the tissue. For this an electrode 22 is provided on the distal end 14 of the working instrument 3 that is connected to the connection conductor 19. Here the electrode 22 is illustrated as pin-shaped or tube-shaped ignition electrode, but can have arbitrary shapes, e.g. the shape of an ignition platelet. Also the electrode 22 can be arranged on a lug piece or head piece of the working instrument that is not illustrated, that can be made of ceramic, for example, in order to withstand the heat application due to the ignited plasma discharge during use.

Figure 2:
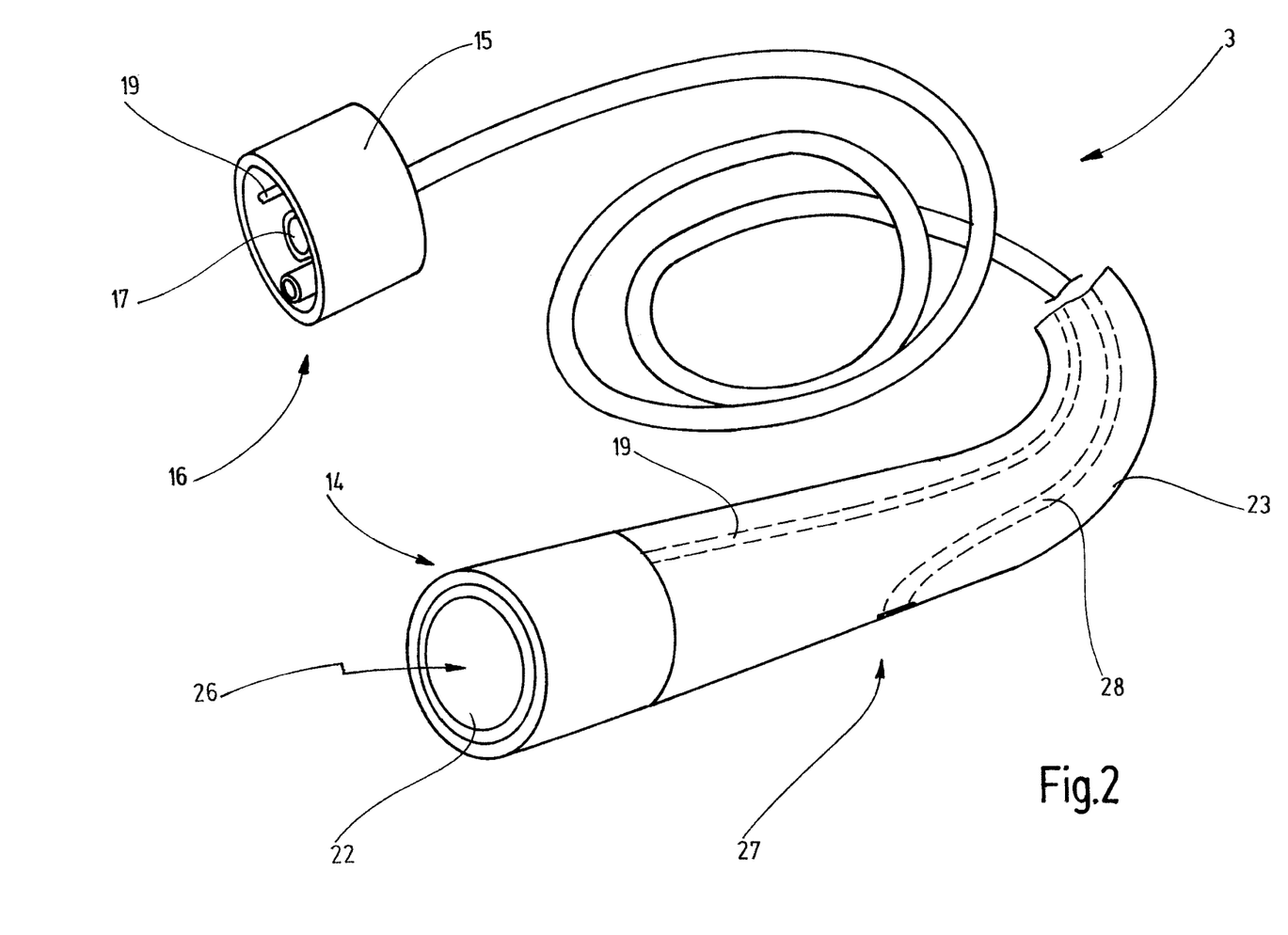
FIG. 2 the working instrument of FIG. 1 in an isolated highly schematic perspective illustration.
Figure 3:
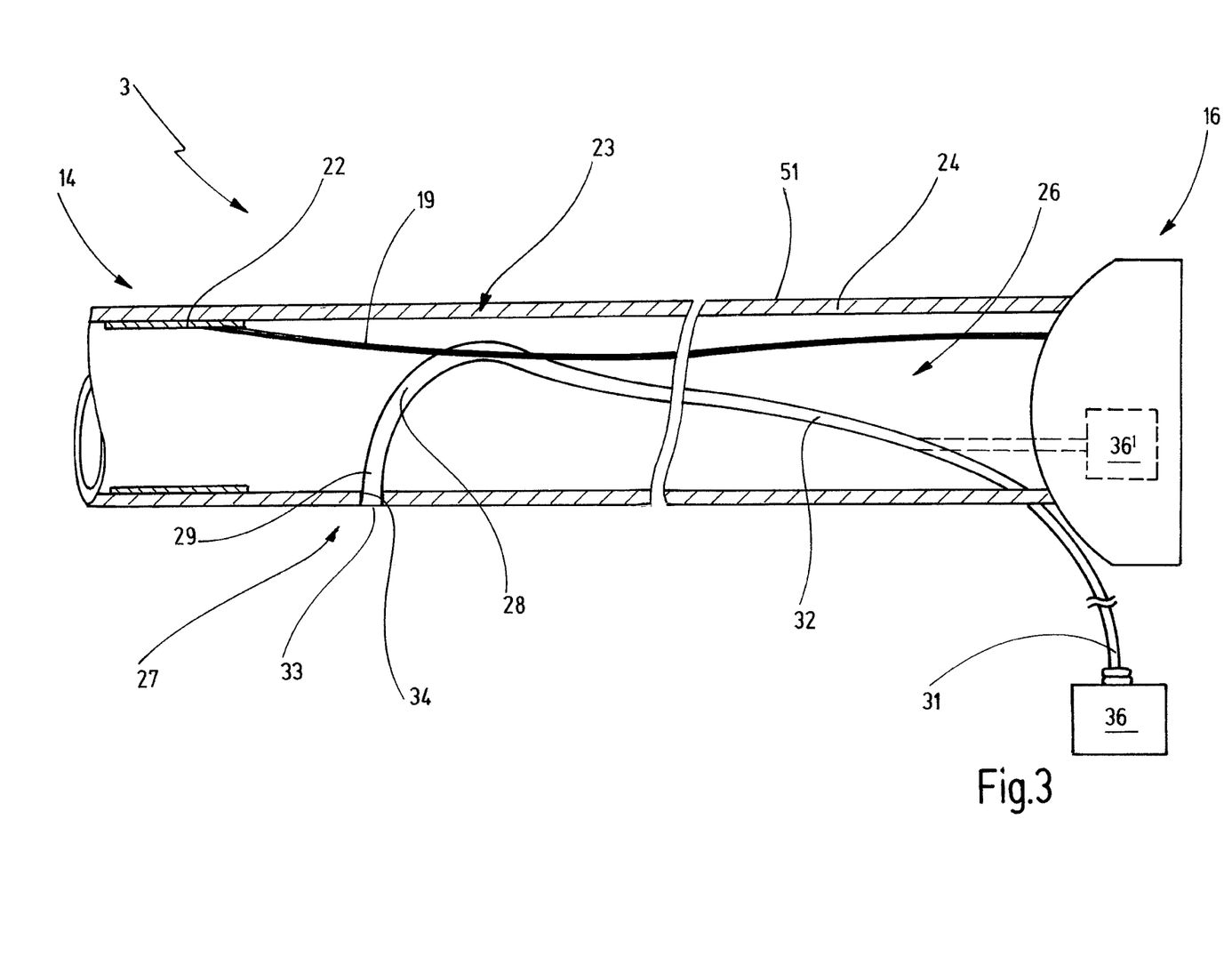
FIG. 3 a longitudinal section through the working instrument of FIGS. 1 and 2 in simplified illustration.

The surgical working instrument 3 is shown in FIG. 2 in an isolated simplified perspective view and in a schematic longitudinal sectional illustration in FIG. 3. As illustrated, the working instrument 3 that can also be denoted as probe, comprises a tube 23 that is configured as flexible hose here and is made of a suitable biocompatible material appropriate for the present applications, particularly PTFE. Basically in a rigid endoscope also a rigid tube 23 could be used. The tube 23 comprises a wall 24 that defines a substantially cylindrical inner channel 26 that can also be denoted as lumen, through which the gas, e.g. argon, is supplied to the distal end 14 of the working instrument 3. In the inner channel 26 also the connection conductor 19 is located that extends originating from the proximal end 16 of the working instrument 3 up to its distal end 14 and is connected with the electrode 22 there.

In the argon plasma coagulation it is important to position the electrode 22 of the working instrument 3 during use in suitable relative position in relation to the endoscope 2. Particularly the electrode 22 should be positioned in a minimum distance to the distal end 8 of the endoscope 2 so that after the ignition of the plasma discharge, when the ionized gas serves as conductor for the supply of coagulation current, the heat created thereby does not affect the endoscope 2. For example, the working instrument 3 can be configured for single use such that it can be relatively cheaply produced and is discarded after one endoscopic treatment or surgery. On the contrary, the endoscope with its components is relatively expensive and configured for multiple use. For this reason particularly components arranged on the distal end 8 of the endoscope 2, such as for example the observation device 11, the illumination device 12 and the like, have to be protected against damage because of the heat developed during use. For this a minimum distance between the APC probe tip having the electrode 22 and the distal end 14 of the endoscope of at least about 10 mm is required, e.g. in an APC probe 3 having an outer diameter of about 2-5 mm.

Conversely, the electrode 22 should however also not project too far out of the working channel 7 of the endoscope 2 so that it is arranged in the illumination field of the illumination device 12 and in the field of view of the observation device 11 during use and also that undesired contacts of the tissue surface to be treated by the electrode 22 involving a respective risk of an injury are avoided.

Also in other applications an appropriate relative positioning of the probe tip relative to the endoscope and should be ensured in order to allow an efficient endoscopic treatment or session or to avoid an undesired contact of an optic or an instrument at the probe tip with the tissue, for example.

In order to allow the desired relative positioning of the working instrument 3 in relation to the endoscope 2 and to monitor the position condition of the active electrode 22, a position determination device 27 is provided. Again referring to FIGS. 2 and 3 the position determination device 27 comprises a light conductor 28 that is attached to the working instrument 3 and configured to receive light that is surrounding the working instrument 3 in the vicinity of its distal end 14, whereby the relative position of the working instrument 3 relative to the endoscope 2 can be determined by means of the light received by means of the light conductor 28.

The light conductor 28 is immovably attached to the working instrument 3 such that it can be inserted and slid in the working channel 7 of the endoscope 1 together with the working instrument 3. Thereby the light conductor can extend originating from a location in the vicinity of the distal end 14 of the working instrument 3 up to the proximal end 16, in order to conduct the light received from the environment for evaluation to the proximal end of the working instrument 3. The light conductor 28 can comprise an arbitrary optical fiber, e.g. glass fiber or preferably a polymer optical fiber. Relatively cheap optical fibers are available that are suitable for the present function of position detection for which no highest qualitative absolutely lossless light reception and transfer is necessary.

Referring again to FIGS. 2 and 3 the light conductor 28 is located in the illustrated embodiment, mainly in the inner channel 26 of the working instrument 3. The light conductor 28 comprises a first end 29 that is attached to the tube 23 of the working instrument 3, a second end 31 that extends beyond the proximal end 16 of the tube 23 and a light conductor central section 32 extending therebetween that is substantially located in the inner channel 26. The first end 29 of the light conductor 28 extends through the wall 24 of the tube 23 and comprises a face 33 that is orientated radially or laterally to the outward relative to the longitudinal axis of the working instrument 3 that is not illustrated here. The face 33 forms a light entering surface in order to receive outside light at the outer side of the tube 23 and to guide it in the light conductor 28. The received light is then transmitted via the light conductor central section 32 to the second end 31.

The first end 29 of the light conductor 28 is located in an opening 34 that is introduced in the flexible tube 23 with matching shape and can be secured therein additionally, e.g. by means of gluing. The face 33 of the light conductor 28 serving as light entering surface ends preferably substantially flush with the outer side of the tube 23. The tube 23 itself consists of an opaque material.

The second end 31 of the light conductor 28 is connected with an evaluation device 36 that can be connected or is connected to the proximal end 16 of the working instrument 3 and is configured to receive and evaluate the light received by the light conductor 28 in order to determine the relative position of the working instrument 3. Embodiments of the evaluation device 36 are illustrated in simplified block diagram illustrations in FIGS. 4a and 4b.

Figure 4A:
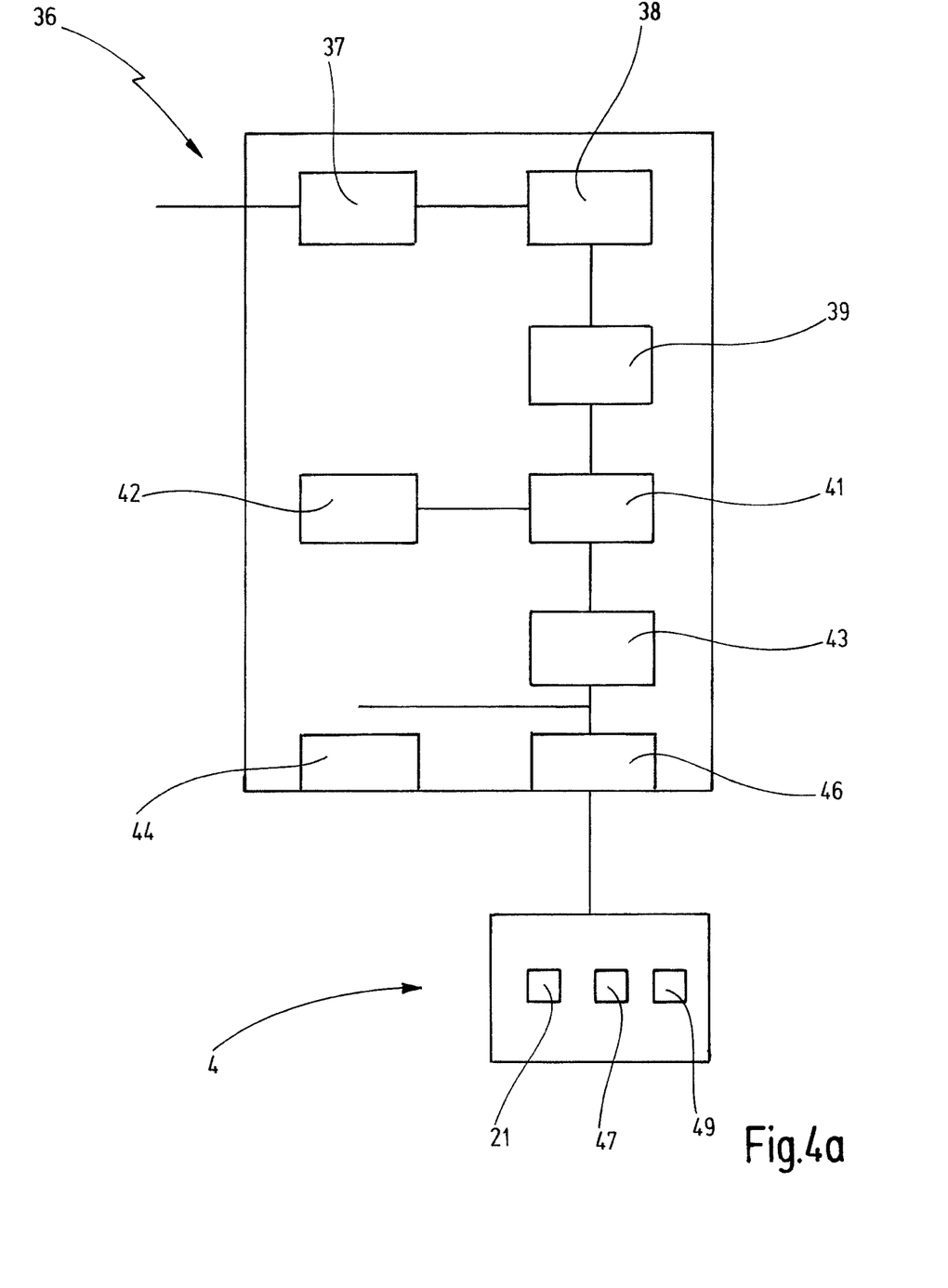
FIGS. 4a and 4b embodiments of evaluation devices for the working instruments of FIGS. 1 to 3 in simplified block diagrams.

Referring to FIG. 4a the evaluation device can comprise in a first embodiment a spectrometer unit 37 and electrooptical converter 38, a signal conditioning unit 39, a spectrum analyzing unit 41, a storage 42, a detector unit 43, an output unit 44 and an interface 46. Although the units 37 to 46 are illustrated as separate blocks here, they only form functional units that can be comprised in one or more physical units, can be distributed on individual units, can be realized in hardware and/or software and can be at least partly embodied by a logic that can be implemented in the form of a code for execution on a processor that is not illustrated here, in order to fulfill the function of the evaluation device 36 for evaluation of light received by the light conductor 28 and for determination of the relative position of the instrument 3.

The spectrometer unit 37 is connected with the light conductor 28 in order to receive the received light therefrom and divides the light spectrally in individual frequency components. The spectrometer unit 37 can comprise a light refracting prism or a light diffracting grid, for example. If necessary the resulting light can be filtered before it is supplied to the electrooptical converter 38. The electrooptical converter 38 that can also be a photodiode array converts the spectrally divided light in respective electrical signals for subsequent evaluation and analysis in order to determine the frequency spectrum of the received light signals. In the signal conditioning unit 39 the obtained electrical signals can be amplified, filtered from interfering signals, e.g. low pass or band pass filtered and conditioned otherwise for the further processing.

The spectrum analyzing unit 41 is configured to evaluate the electrical signals that represent the spectrally divided light components in order to determine the spectral components of the light or the intensities of the light in different light frequency ranges or at the defined discrete frequencies and compare them with stored reference spectra in order to classify or identify the light received by the light conductor based on the comparison. The reference spectra can be determined in advance and can be stored beforehand in the storage 42. A reference spectrum for the cold light of the endoscope 3, for the ambient light of a workroom, as well as for the plasma light resulting from the spark discharge during the APC coagulation can be stored. All these light sources comprise characteristic spectra that remarkably distinguish from one another with reference to the respective frequency range and the intensity values therein. For example, an ambient light of a workroom will comprise wavelengths in the range of 300 nm to 1100 nm with a characteristic first intensity distribution, whereas the working light from a cold light source of the endoscope generally comprises a wavelength range of 400 nm to 700 nm or a sub-range therein and a second characteristic intensity distribution and the light emitted from the plasma comprises characteristic components in the visible wavelength range as well as also in the range of 200 nm to 400 nm with a different third intensity distribution.

One or more of the ambient light, the cold light of the endoscope and/or the light emitted from the plasma can also be detected empirically in order to determine and store the assigned reference spectra therefrom. Alternatively, also representative frequency spectra obtained from the manufacturers of the respective illumination or apparatus or simulated light spectra can be used as reference spectra. In any case, the spectrum analyzing unit 41 is able to determine based on a comparison of intensity values of specific discrete frequency lines or frequency ranges in different frequency bands whether light was received by means of the light conductor 28 or not and if so, whether it is cold light of the illumination device 12 of the endoscope 2, ambient light of the examination or treatment room or a light signal based on spark discharge.

The detector unit 43 monitors the light type identified by the spectrum analyzing unit and is configured to recognize during insertion of the working instrument 3 in the working channel 7 of the endoscope 2 when the light entering surface, particularly the face 33 of the light conductor 28, is subject to the environment of the treatment room, enters from the environment in the proximal end 13 of the working channel 7 or exits from the working channel 7 in a body area to be treated. Based on this recognition, the detector unit 43 generates respective position detection signals that, for example, characterize the beginning of the insertion of the working instrument 3 in the working channel 7 or indicate that the distal end 14 of the instrument 3 extends beyond the distal end 8 of the endoscope 2 by the desired distance that corresponds to the distance between the distal end 14 of the working instrument 3 and the light entering surface 33.

The optional output unit 44 can be connected with the detector unit 43 in order to receive the position detection signals therefrom and to convert them in optical, acoustic or tactile indication signals that can be recognized by a user of the surgical working instrument 3. Thus, the user is able to recognize when the working instrument 3 is positioned in the desired relative working position in relation to the endoscope 2.

As an alternative or in addition, the detector unit 43 can be connected with the control apparatus 4 of the endoscope system 1 via the interface 46, wherein the control apparatus 4 can receive the position detection signals from the detector unit 43 and can automatically initiate appropriate measures based thereon, e.g. it can effectuate an activation lock, a pre-activation, a parameterization and/or a control of the operation of the working instrument 3 and/or the endoscope 2.

Figure 4B:
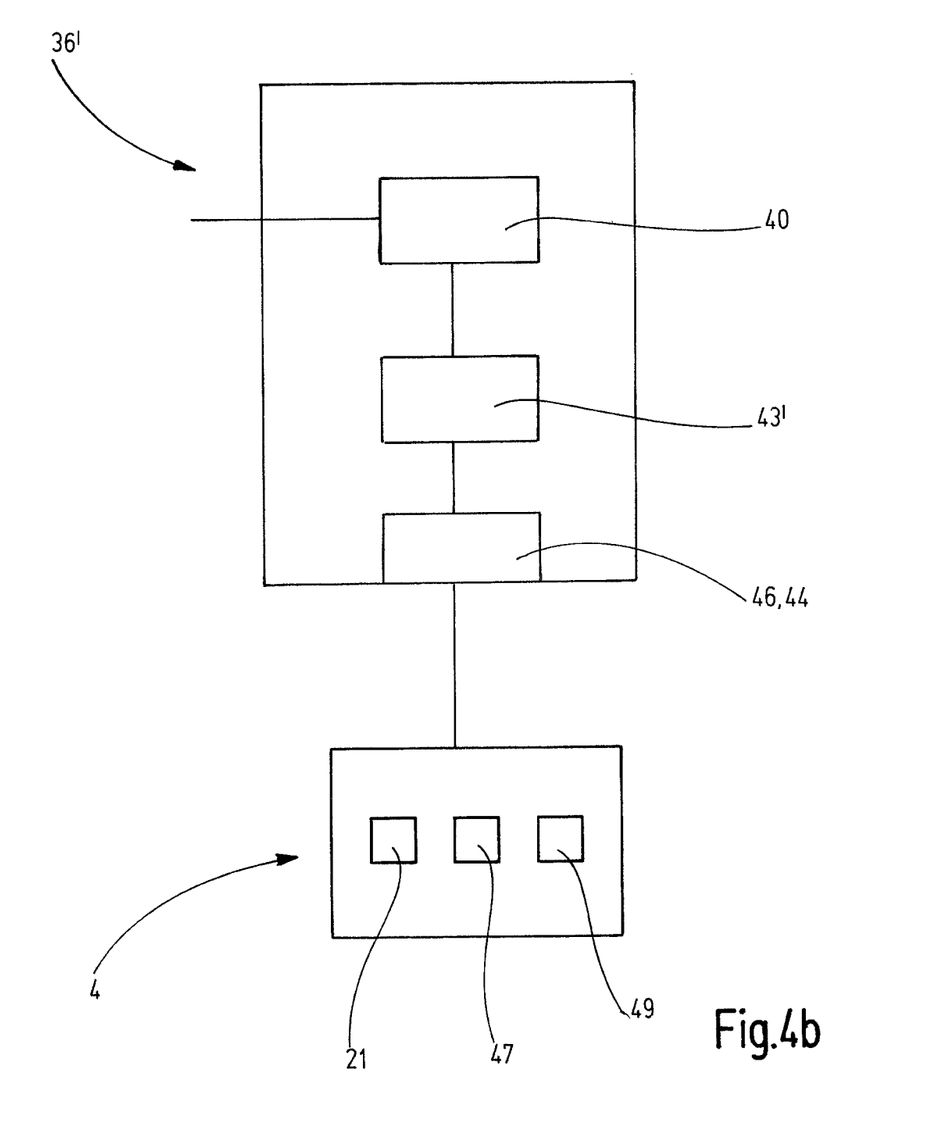

FIG. 4b shows another particularly preferred embodiment of an evaluation device 36' that is realized in a very complex-poor manner and can be configured to a highly simplified evaluation of the light received by the light conductor 28 for cause position determination. Particularly the evaluation device 36' allows only the determination of the presence or absence of received light or a light-dark differentiation. As apparent from FIG. 4b, in this case the evaluation device 36' can comprise a means 40 for conversion of the received light signal in an electrical signal, particularly a photodiode, and a detector unit 43' that forms a light-dark detector. The detector unit 43' can preferably compare the strength of the electrical signal created by the photodiode or the like with a pre-defined threshold in order to determine whether the light received by the light conductor 28 has a minimum intensity or not and based thereon generate position detection signals that characterize whether the distal end 14 of the working instrument 3 is subject to light (light) or not (darkness), i.e. is located for example outside or inside the working channel 7 of the endoscope 2. Thus, light-dark or dark-light transitions can be detected. A user or a superordinate control in the external control apparatus 4 can then determine in which relatively coarse position the working instrument 3 is based on the actual operation condition. A distinction between the different types of light and a more precise position determination are not necessary here. In so far, the functional units 37-41 for the frequency spectrum determination and analysis can be omitted here. The interface 44, 46 illustrated additionally in FIG. 4*b*, can be a connection line, a plug-in or a connection socket in the simplest case.

Figure 5A:
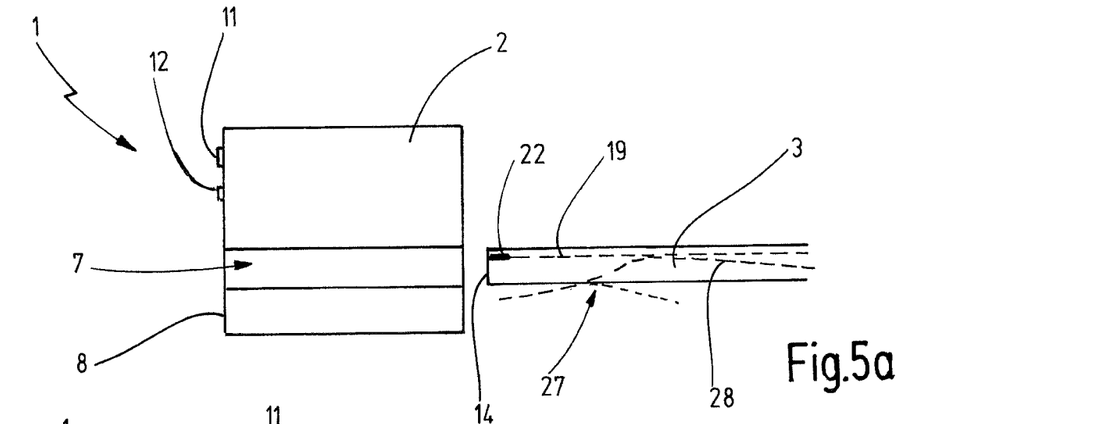
FIGS. 5a to 5c simplified principle illustrations of the endoscope and the working instrument in different relative positions with regard to one another for illustration of the function.

The function of the inventive endoscope system 1 described so far shall be explained in the following with additional reference to FIGS. 5*a* to 5*c* in which the function progress with the respective relative positions of the working instrument 3 in relation to the endoscope 2 are individually illustrated. The endoscope system 1 functions as follows:

If an argon plasma coagulation shall be carried out, the user of the control apparatus 4 can select the desired mode, whereby components of the endoscope system 1 including the position determination device 27 can be activated. The position determination device 27 determines by means of the light received by the light conductor 28 after evaluation by means of the evaluation device 36 or 36' that the probe 3 is still located outside the endoscope 2, as illustrated in FIG. 5*a* and subject to the ambient light of the treatment room. The detector unit 43 determines, for example, that the determined frequency spectrum of the received light corresponds with the reference spectrum of the ambient light at least at distinct discrete frequencies, however, remarkably distinguishes from the reference spectra of the cold light source of the endoscope 2 and the light signal emitted by the plasma and indicates a corresponding position signal via the interface 44 or 46. Alternatively, the light-dark detector unit 43' indicates a signal characterizing the light condition. As far as position signals are mentioned, this also means the light and dark signals generated by the light-dark detector device 40, 43'.

Figure 5B:
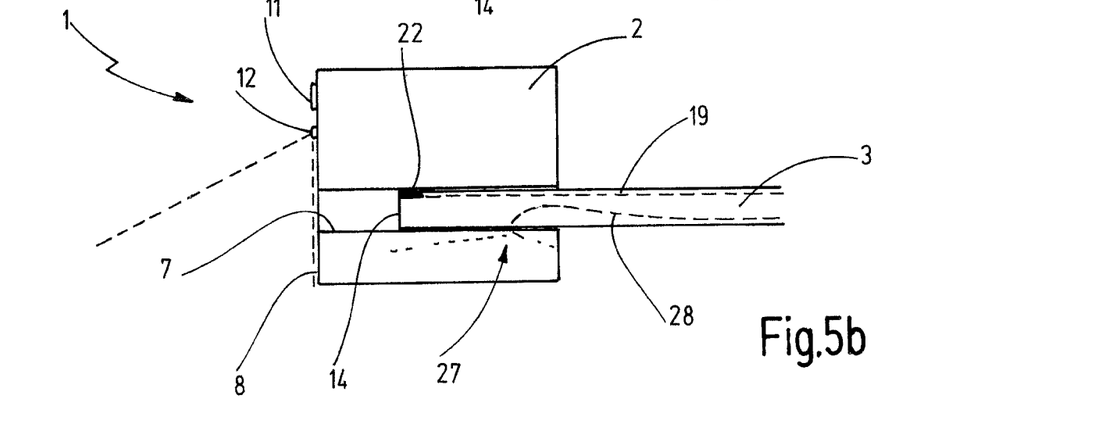

If the user subsequently introduces the working instrument 3 in the proximal end 13 of the endoscope 2 and the face 33 of the light conductor 28 enters the working channel 7, as illustrated in FIG. 5*b*, the intensity of the light received by the light conductor 28 drops relatively suddenly. In the inside of the working channel 7 absolute darkness prevails. The absence of the received light signal can be determined quickly and reliably by the evaluation unit 36 or 36', whereupon the detector unit 43 or 43' can output a respective darkness signal to the output unit 44 and/or to the control apparatus 4. Thereupon the control apparatus 4 can effectuate, provided it hasn't already happened, a pre-activation of the endoscope system 1, including a parameterization of the RF-generator device 21, switching on the illumination device 12 and pre-adjustment of control valves for the gas supply. In some applications the inert gas supply can already be started as soon as it is recognized that the working instrument 3 is inserted in the working channel 7 in order to allow to keep the working instrument 3 clean during the insertion process.

Figure 5C:
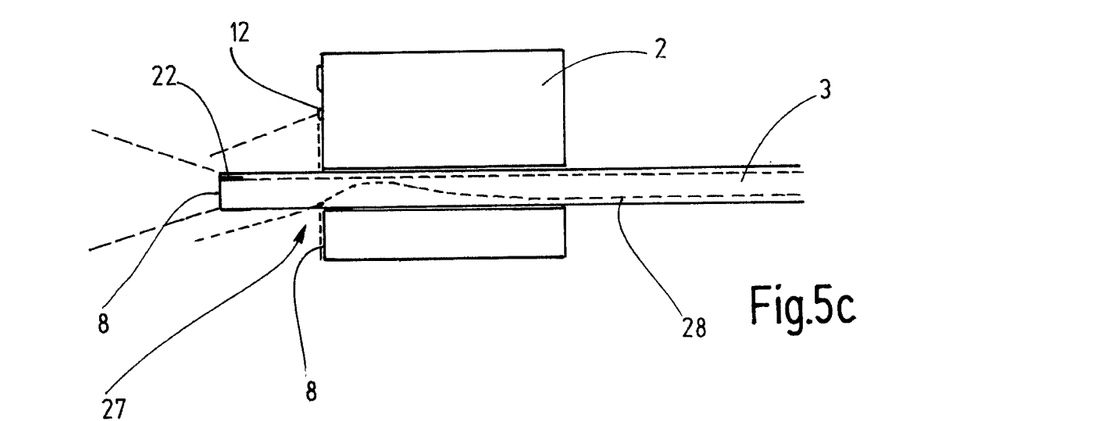

As soon as the distal end 14 of the probe 3 exits the distal end 8 of the endoscope 2 so far that the face 33 of the light conductor 28 leaves the working channel 7, as illustrated in FIG. 5*c*, the face 33 receives working light that is emitted from the illumination device 12 on the distal end 8 of the endoscope 2 for illumination of the treatment or surgery area. This light is supplied by a suitable cold light source 47 that can be, for example, integrated in the control apparatus 4 or also in an external light source. The evaluation device 36 or 36' of the position determination device 27 receives the light signal via the light conductor 28 and recognizes the sudden change between absent and actual light signal. For example, the light-dark detector unit 43' determines the dark-light transition and indicates again a signal characterizing the light condition. As an alternative, the spectrum analyzing unit 41 in the evaluation unit 36 can analyze the frequency spectrum of the received light and determine that the received light is working light, i.e. the cold light of the endoscope 2, by referring to the reference spectra stored in the storage 42. By means of the output unit 44 the detector unit 43 or 43' can output the respective position detection signal for the user that hence can recognize that the probe tip with the electrode 22 has now reached the desired position, such that the working instrument 3 should not be advanced further.

The position detection signal can be alternatively or additionally transmitted to the control apparatus 4 via the interface 46 that thereupon can cancel the activation lock for the electrical RF-signal and also can already start with the control of the operation of the working instrument 3 automatically. For example, provided it hasn't already happened, the supply of the gas to be ionized, e.g. argon, to the working instrument 3 can be initiated and the ignition of a plasma discharge by the electrode 22 can be allowed automatically. Thus, the RF-generator device 21 can supply the required RF-voltage signal to the electrode 22 via the connection conductor 19 in order to allow an ignition of the plasma discharge and ionization of the gas, whereupon the created argon plasma is used as current conductor in order to transfer the coagulation current on the tissue to be treated. By means of the optic 11, e.g. a CCD camera, the treated area can be captured and the image signals can be supplied via an optic fiber 48 to an image processing unit 48 of the control apparatus 4 in order to be displayed to the user on a display that is not illustrated here.

If the user retracts the working instrument 3 unintentionally or intentionally so far that the face 33 of the light conductor 28 enters the working channel 7, this is determined by the evaluation device 36 or 36' of the position determination device 27. The control apparatus 4 can then automatically stop the operation of the working instrument 3 and effectuate an activation lock in order to interrupt the gas and/or RF-voltage supply, such that the spark discharge is suspended and damage of the endoscope 2 is avoided.

The action of repeatedly sliding the working instrument 3 in and out of the working channel 7 could also be specifically carried out by the user in order to identify the exact location of the desired working position for the working instrument 3. In so far, the activation or suspension of the activation lock can be delayed as long as the user still carries out adjustments.

In the context of the invention numerous modifications are possible. The evaluation device 36 or 36' can be contained in an apparatus unit separate from the working instrument 3, e.g. in the control apparatus 4. Alternatively, parts of the evaluation device 36 or 36', e.g. parts that are realized in hardware, can be located in the connector 15 that forms the interface to the external control apparatus 4, while other parts, particularly parts of the evaluation device 36 or 36' realize in firmware or software, can be implemented, for example, in the control apparatus 4 or in another external apparatus.

In a particularly preferred embodiment, as outlined in dashed lines in FIG. 3, the evaluation device 36' according to FIG. 4b, having the detector device formed by the photodiode 40 and the light-dark detector unit 43' can be completely located in the connector 15 that is arranged on the proximal end 16 of the working instrument 3 and serves for connection with the control apparatus 4. In doing so, an extremely compact and mainly individual unit consisting of the working instrument 3 and the assigned position determination device 27 can be provided that is well suited for use as single use probe, because a complex-poor, relatively cheap detector device 40, 43' can also be disposed after single use.

In another modification the light-dark detector device of the evaluation device 36' according to FIG. 4b integrated in the connector 15 can only comprise the photodiode 40 or another means for conversion of the received light in an electrical signal. The electrical signal can then be transmitted to the external control apparatus 4 via the interface 46 for threshold filtering and/or evaluation. The function of the light-dark detector unit 43' in FIG. 4b can be shifted to the control apparatus 4, which further reduces efforts and costs for the evaluation device 36' installed in the connector 15.

Figure 6:
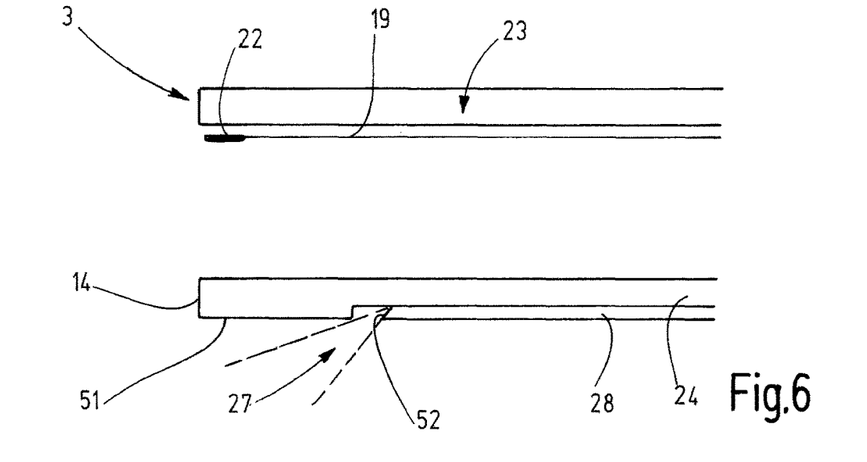
FIG. 6 another embodiment of a working instrument according to the invention in highly schematic longitudinally sectional illustration and FIGS. 7a and 7b another embodiment of a working instrument according to the invention in highly schematic longitudinally sectional illustrations in different relative positions to an endoscope.
Figure 7A:
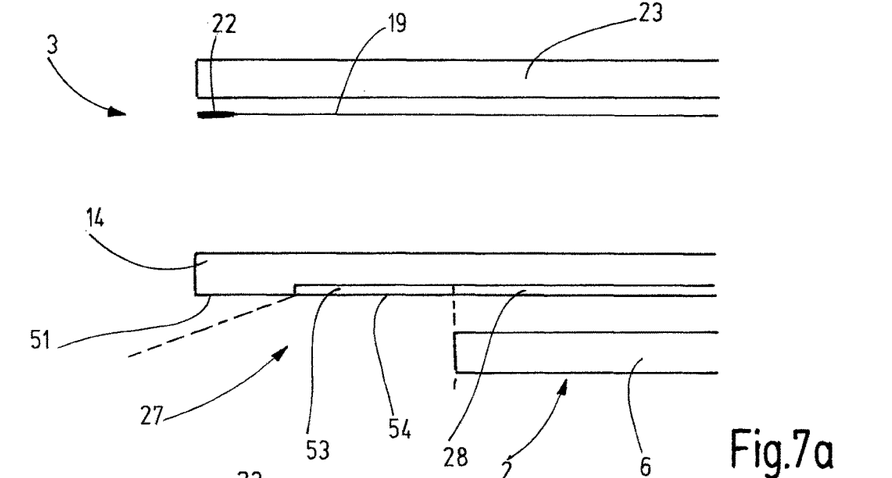
Figure 7B:
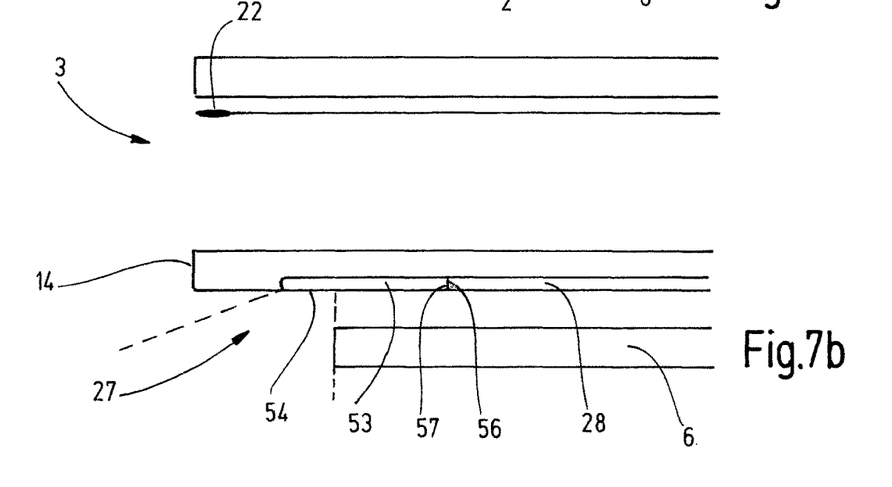

Additional embodiments of the inventive position determination device 27 are illustrated in FIGS. 6 and 7a, 7b. As far as they correspond with the configuration and/or type of function, reference is made on the above description on the basis of the same reference signs.

FIG. 6 shows an embodiment in which the light conductor 28 is not arranged in the inner channel 26 of the tube 23 of the working instrument 3, but on the outer side 51 of the wall 24. The light conductor 28 can comprise a beveled face or fiber bevel 52 that serves as light entering surface in order to receive the surrounding light at the distal end 14 of the working instrument 3 and guide it in the optical fiber central section 32 that guides the light further to the proximal end 16 of the working instrument 3 for evaluation. The beveled face 52 is orientated radially or laterally to the outward as well as in longitudinal direction of the instrument 3, preferably toward the distal end 14. The central section 33 of the light conductor 28 extends originating from the beveled face 52 substantially linearly along the tube 23 at its outer side 51 and can be attached on the outer side 51, e.g. by gluing. Basically it is also possible to arrange the light conductor 28 in the outer side 51 of the tube 23 substantially flush, in that an optical fiber is embedded therein already during extrusion of the hose 23 of the working instrument 3. Independent from how the light conductor 28 is attached on the outer side of the wall 24 of the hose 23, the attachment on the outer side is simplified compared with the arrangement in the inner channel 26 of the working instrument. The function of the position determination device 27 in the embodiment according to FIG. 6 corresponds to the function as described in connection with FIGS. 1 to 5 above.

FIGS. 7a and 7b show a yet further embodiment of the position determination device 27 according to the invention, wherein here the light entering surface for receiving light surrounding the working instrument 3 is formed by a separate light receiving element, namely a longitudinal glass rod 53 in the illustrated example. The glass rod 53 that can be made of silicate glass or acrylic glass is arranged on the outer side 51 of the tube 23 and attached thereon and/or embedded therein. In any case, the longitudinal glass rod 53 comprises a length that is longer than its width and is orientated along the longitudinal extension of the working instrument 3. The length of the glass rod 53 is arbitrary, preferably longer than the half projection length of the distal end 14 of the working instrument 3 in the desired working position or than the distance between the distal end 14 of the working instrument 3 and the distal end of the glass rod 53. The outer surface 54 of the glass rod 53 facing radially or laterally outward serves as light entering surface. A face end 56 of the glass rod 53 facing away from the distal end 14 of the working instrument 3 is connected with a face end 57 of the light conductor 28, such that light received by the glass rod 53 is transferred into the light conductor 28 and through it further to the proximal end 16 of the working instrument 3.

The function of the working instrument 3 and the position determination device 27 in the embodiment according to FIGS. 7a, 7b corresponds mainly to the function of the embodiments described above, wherein however here a more precise determination of the relative position of the working instrument 3 in relation to the endoscope 2 is possible. For example, FIG. 7a shows the condition of the desired positioning of the working instrument 3, in which the distal end 14 of the working instrument 3 projects so far from the working channel 7 that the electrode 22 is in the desired distance to the distal end 8 of the endoscope 2. In this case also the glass rod 53 is completely slid out of the working channel 7, such that a light signal with high intensity is received by the light conductor 28 and supplied to the position determination device 27. The evaluation device 36 or 36' recognizes the light signal of maximum intensity, e.g. based on a maximum of multiple thresholds and thereupon creates a position detection signal that indicates that the working instrument 3 is now located in the desired working position.

In FIG. 7b a condition is illustrated in which the distance of the distal end 14 or the electrode 22 of the working instrument 3 to the distal end 8 of the endoscope 2 is smaller than the desired distance. This condition can occur either during insertion of the working instrument 3 in the working channel 7 in preparation to an APC coagulation or another endoscopic treatment or examination or during operation, if the user, e.g. unintentionally, retracts the working instrument 3 at least partly in the working channel 7 again. The tube 6 of the endoscope 2 covers in this case at least a section of the outer surface 54 of the glass rod 53 such that only a reduced amount of light is received by the glass rod 53 and is introduced in the light conductor 28. The evaluation device 36 or 36' recognizes the reduced intensity of the received light and can in this case, for example, initiate or maintain the activation lock in order to avoid that in case of an ignition of the plasma discharge, due to the proximity of the electrode 22 to the endoscope 2 or its components is or are damaged.

A surgical working instrument 3 is disclosed that is inserted in a working channel 7 of an endoscope 2 and is slidably located therein. A device 27 for determination of the relative position of the working instrument 3 to the endoscope 2 is configured to determine in an optical manner that the distal end 8 of the working instrument 3 has reached a distal end 8 of the working channel 7. The position determination device 27 comprises a light conductor 28 that is attached to the working instrument 3 and configured to receive light surrounding the working instrument 3 in the vicinity of its distal end 14, wherein based on the light received by the light conductor 28 the relative position of the light conductor 28 and thus the working instrument 3 in relation to the endoscope 2 can be determined.

The invention claimed is:

1. A surgical working instrument (3) for insertion in a working channel (7) of an endoscope (2), the surgical working instrument comprising:

a position determination device (27) configured to determine a relative position of the surgical working instrument (3) relative to the endoscope (2), and a tube (23), wherein the position determination device (27) comprises a light conductor (28) that is attached to the surgical working instrument (3) and is configured to receive light surrounding the surgical working instrument (3) in a vicinity of a distal end (14) thereof, wherein the relative position of the surgical working instrument (3) relative to the endoscope (2) is determined based on the light received by the light conductor (28), wherein the position determination device (27) comprises a light entering surface (33, 52, 54) that is arranged on an outer side of the tube (23) and is configured for lateral light reception of the light surrounding the distal end (14) of the surgical working instrument (3), wherein the light entering surface is formed by a face (33) of the light conductor (28) guided laterally out of the tube (23), wherein the light conductor (28) extends inside of the tube (23) substantially along a longitudinal extension thereof.

2. The surgical working instrument (3) according to claim 1, wherein the light conductor (28) comprises an optical fiber formed of a glass or plastic material, that is attached to the surgical working instrument (3) such that during insertion of the surgical working instrument, the optical fiber is inserted and slid in the working channel (7) of the endoscope (2) together with the surgical working instrument (3).

3. The surgical working instrument (3) according to claim 1, wherein the light conductor (28) extends from a location in the vicinity of the distal end (14) of the surgical working instrument (3) to a proximal end (16) of the surgical working instrument (3) in order to transmit light received by the light conductor (28) to the proximal end (16) of the surgical working instrument (3) for evaluation.

4. The surgical working instrument (3) according to claim 1, further comprising an evaluation device (36, 36') that is connected to a proximal end (13) of the surgical working instrument (3) and is configured to receive and evaluate light received by the light conductor (28).

5. The surgical working instrument (3) according to claim 4, wherein the evaluation device (36) comprises an optical spectrometer unit (37) that is configured to divide the received light into its spectral components.

6. The surgical working instrument (3) according to claim 5, wherein the evaluation device (36) comprises a spectrum analyzing unit (41) that is configured to compare a determined intensity of the received light over a range of light frequencies or in certain discrete frequencies with stored reference spectra and is further configured to identify the light received by the light conductor (28) based on the comparison, wherein the spectrum analyzing unit (41) is configured to at least distinguish between treatment room ambient light, darkness, and treatment light from the endoscope (2).

7. The surgical working instrument (3) according to claim 4, wherein the evaluation device (36) comprises a detector unit (43) that is configured to determine during insertion of the surgical working instrument (3) in the working channel (7) when the light entering surface (33, 52, 54) is subject to an environment of a treatment room, enters into the working channel (7), or exits out of the working channel (7) in a body region to be treated and is further configured to generate corresponding position determination signals based thereon.

8. The surgical working instrument (3) according to claim 4, wherein the evaluation device (36') comprises a detector (40, 43') that is configured to determine whether light received by the light conductor (28) has a minimum intensity and is configured to generate corresponding position determination signals based thereon.

9. The surgical working instrument (3) according to claim 7, wherein the evaluation device (36, 36') is integrated in a connector (15) that is arranged on a proximal end (16) of the surgical working instrument (3) and is configured for connection with an external control apparatus (4).

10. The surgical working instrument (3) according to claim 7, wherein the evaluation device (36, 36') is configured to be connected with a control (4) for the surgical working instrument (3) and/or the endoscope (2) that is configured to automatically effectuate one or more of the following measures based on the position determination signals: release or block activation of an electrical signal supplied via the surgical working instrument (3), release or block a gas flow through the surgical working instrument (3), and parameterize and/or control an operation of the surgical working instrument (3) and/or the endoscope (2) in a desired working position.

11. The surgical working instrument (3) according to claim 1, wherein the surgical working instrument is a coagulation probe (3) for RF-coagulation of biological tissue, wherein the endoscope (2) is flexible, wherein the coagulation probe (3) comprises the tube (23) in the form of a flexible hose made of an electrically non-conductive material through which an inert gas is supplied and further comprises an electrode (22) arranged on a distal end (14) of the tube (23), to which an RF-coagulation current is supplied via a connection conductor (19) for ionization of the inert gas.

12. A surgical working instrument (3) for insertion in a working channel (7) of an endoscope (2), the surgical working instrument comprising:

a position determination device (27) configured to determine a relative position of the surgical working instrument (3) relative to the endoscope (2), and a tube (23), wherein the position determination device (27) comprises a light conductor (28) that is attached to the surgical working instrument (3) and is configured to receive light surrounding the surgical working instrument (3) in a vicinity of a distal end (14) thereof, wherein the relative position of the surgical working instrument (3) relative to the endoscope (2) is determined based on the light received by the light conductor (28), wherein the position determination device (27) comprises a light entering surface (33, 52, 54) that is arranged on an outer side of the tube (23) and is configured for lateral light reception of the light surrounding the distal end (14) of the surgical working instrument (3), wherein the light entering surface is formed by a beveled face (52) of the light conductor (28), wherein the light conductor (28) is attached to the outer side of the tube (23) and extends along a longitudinal extension of the tube.

13. The surgical working instrument (3) according to claim 12, wherein the light conductor (28) comprises an optical fiber formed of a glass or plastic material, that is attached to the surgical working instrument (3) such that during insertion of the surgical working instrument, the optical fiber is inserted and slid in the working channel (7) of the endoscope (2) together with the surgical working instrument (3).

14. The surgical working instrument (3) according to claim 12, wherein the light conductor (28) extends from a location in the vicinity of the distal end (14) of the surgical working instrument (3) to a proximal end (16) of the surgical working instrument (3) in order to transmit light received by the light conductor (28) to the proximal end (16) of the surgical working instrument (3) for evaluation.

15. The surgical working instrument (3) according to claim 12, further comprising an evaluation device (36, 36') that is connected to a proximal end (13) of the surgical working instrument (3) and is configured to receive and evaluate light received by the light conductor (28).

16. The surgical working instrument (3) according to claim 15, wherein the evaluation device (36) comprises an optical spectrometer unit (37) that is configured to divide the received light into its spectral components; and
wherein the evaluation device (36) comprises a spectrum analyzing unit (41) that is configured to compare a determined intensity of the received light over a range of light frequencies or in certain discrete frequencies with stored reference spectra and is further configured to identify the light received by the light conductor (28) based on the comparison, wherein the spectrum analyzing unit (41) is configured to at least distinguish between treatment room ambient light, darkness, and treatment light from the endoscope (2).

17. The surgical working instrument (3) according to claim 15, wherein the evaluation device (36) comprises one of:
a detector unit (43) that is configured to determine during insertion of the surgical working instrument (3) in the working channel (7) when the light entering surface (33, 52, 54) is subject to an environment of a treatment room, enters into the working channel (7), or exits out of the working channel (7) in a body region to be treated and is further configured to generate corresponding position determination signals based thereon; or
a detector (40, 43') that is configured to determine whether light received by the light conductor (28) has a minimum intensity and is configured to generate corresponding position determination signals based thereon.

18. A surgical working instrument (3) for insertion in a working channel (7) of an endoscope (2), the surgical working instrument comprising:
a position determination device (27) configured to determine a relative position of the surgical working instrument (3) relative to the endoscope (2), and
a tube (23),
wherein the position determination device (27) comprises a light conductor (28) that is attached to the surgical working instrument (3) and is configured to receive light surrounding the surgical working instrument (3) in a vicinity of a distal end (14) thereof,
wherein the relative position of the surgical working instrument (3) relative to the endoscope (2) is determined based on the light received by the light conductor (28),
wherein the position determination device (27) comprises a light entering surface (33, 52, 54) that is arranged on an outer side of the tube (23) and is configured for lateral light reception of the light surrounding the distal end (14) of the surgical working instrument (3),
wherein the light entering surface is formed by an outer surface (54) of a longitudinal glass rod (53) that is arranged on the outer side of the tube (23), such that a longitudinal extension of the glass rod is oriented in a longitudinal direction of the working instrument (3) and a face end (56) of the glass rod facing away from the distal end (14) of the surgical working instrument (3) is connected with the light conductor (28).

19. The surgical working instrument (3) according to claim 18, wherein the light conductor (28) comprises an optical fiber formed of a glass or plastic material, that is attached to the surgical working instrument (3) such that during insertion of the surgical working instrument, the optical fiber is inserted and slid in the working channel (7) of the endoscope (2) together with the surgical working instrument (3).

20. The surgical working instrument (3) according to claim 18, wherein the light conductor (28) extends from a location in the vicinity of the distal end (14) of the surgical working instrument (3) to a proximal end (16) of the surgical working instrument (3) in order to transmit light received by the light conductor (28) to the proximal end (16) of the surgical working instrument (3) for evaluation.

21. The surgical working instrument (3) according to claim 18, further comprising an evaluation device (36, 36') that is connected to a proximal end (13) of the surgical working instrument (3) and is configured to receive and evaluate light received by the light conductor (28).

22. The surgical working instrument (3) according to claim 21, wherein the evaluation device (36) comprises an optical spectrometer unit (37) that is configured to divide the received light into its spectral components, and
wherein the evaluation device (36) comprises a spectrum analyzing unit (41) that is configured to compare a determined intensity of the received light over a range of light frequencies or in certain discrete frequencies with stored reference spectra and is further configured to identify the light received by the light conductor (28) based on the comparison, wherein the spectrum analyzing unit (41) is configured to at least distinguish between treatment room ambient light, darkness, and treatment light from the endoscope (2).

23. The surgical working instrument (3) according to claim 21, wherein the evaluation device (36) comprises one of:
a detector unit (43) that is configured to determine during insertion of the surgical working instrument (3) in the working channel (7) when the light entering surface (33, 52, 54) is subject to an environment of a treatment room, enters into the working channel (7), or exits out of the working channel (7) in a body region to be treated and is further configured to generate corresponding position determination signals based thereon; or
a detector (40, 43') that is configured to determine whether light received by the light conductor (28) has a minimum intensity and is configured to generate corresponding position determination signals based thereon.

* * * * *